(12) United States Patent
Okazaki et al.

(10) Patent No.: US 7,300,747 B2
(45) Date of Patent: Nov. 27, 2007

(54) PHOTOBASE GENERATOR AND CURABLE COMPOSITION

(75) Inventors: Hitoshi Okazaki, Tokyo (JP); Junya Hayakawa, Tokyo (JP); Motoharu Takeuchi, Tokyo (JP); Masahiro Jono, Tokyo (JP); Kenji Ishii, Tokyo (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 153 days.

(21) Appl. No.: 11/050,740

(22) Filed: Feb. 7, 2005

(65) Prior Publication Data

US 2005/0181300 A1   Aug. 18, 2005

(30) Foreign Application Priority Data

Feb. 16, 2004   (JP) .............................. 2004-039081

(51) Int. Cl.
| | |
|---|---|
| G03C 1/73 | (2006.01) |
| C08G 59/40 | (2006.01) |
| C08G 75/06 | (2006.01) |
| C08G 75/14 | (2006.01) |
| C08L 81/04 | (2006.01) |
| C07D 331/02 | (2006.01) |
| G02B 1/04 | (2006.01) |

(52) U.S. Cl. ...................... 430/920; 430/919; 430/921; 430/923; 430/280.1; 430/270.1; 522/31; 522/33; 522/34; 522/38; 522/39; 522/45; 522/50; 522/54; 522/63; 522/168; 564/282; 564/284; 564/287; 564/288; 564/289; 568/42; 568/43; 568/44; 568/58

(58) Field of Classification Search ...................... None
See application file for complete search history.

(56) References Cited

U.S. PATENT DOCUMENTS 2,759,971 A * 8/1956 Cutler et al. ................ 564/135

6,635,195 B1   10/2003 Wanigatunga et al.

OTHER PUBLICATIONS

Cutler, Royal A. et al., "New antibacterial agents. 2- Acylamino 1-(4-hydrocarbonylsulfonylphenyl)-1, 3-propanediols and related compounds" Journal of the American Chemical Society, vol. 74, 5475-81, 1952.

Tachi, Hideki et al., "Photochemical reactions of quaternary ammonium dithiocarbamates as photobase generators and their use in the photoinitiated thermal crosslinking of poly(glycidyl methacrylate)" Journal of Polymer Science, Part A: Polymer Chemistry; vol. 39(9), 1329-1341, 2001.

Shirai, Masamitsu et al., "Photoacid and photobase generators: chemistry and applications to polymeric materials" Progress in Polymer Science, vol. 21(1), 1-45, 1996.

European Search Report mailed Apr. 25, 2005, for EP 05 10 0487.

* cited by examiner

*Primary Examiner*—Sin Lee
(74) *Attorney, Agent, or Firm*—Antonelli, Terry, Stout & Kraus, LLP.

(57) ABSTRACT

The photobase generator of the invention is represented by the following formula 1:

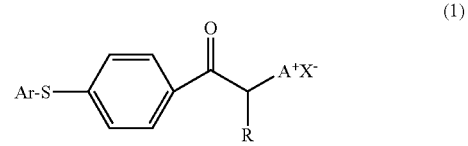

(1)

wherein Ar, R, $A^+$ and $X^-$ are as defined in the specification. Since the photobase generator of the formula 1 absorbs ultraviolet lights of relatively long wavelength and is photolyzed to generate a strong base efficiently, a composition containing the photobase generator and an episulfide compound is easily cured by polymerization under ultraviolet irradiation.

19 Claims, No Drawings

PHOTOBASE GENERATOR AND CURABLE COMPOSITION

BACKGROUND OF THE INVENTION

1. Field of the Invention

The present invention relates to a photobase generator and a curable composition containing the photobase generator which are suitable for producing optical materials such as adhesives for optical devices, coating compositions for optical devices, resist materials, prisms, fiber optics, information recording media, filters and plastic lenses.

2. Description of the Prior Art

Plastic materials are recently finding wide application in various optical materials because of their lightweight, toughness and easiness of dyeing. A high refractive index is one of the characteristic features required for various optical materials. To obtain optical materials having a high refractive index, various episulfide compounds capable of providing optical materials having a refractive index of 1.7 or higher have been proposed (JP 9-71580A, JP 9-110979A and JP 9-255781A). However, most of the raw materials containing the proposed compounds are heat-curable and the resultant optical materials are greatly limited in their application. Therefore, a photo-curable raw material has been strongly demanded.

The photopolymerization of episulfide compounds are reported in U.S. Pat. No. 6,635,195, JP 2002-047346A, JP 2002-105110A, U.S. 2003/0022956 A1 and JP 2003-026806A. In the proposed photopolymerization, radical generators, acid generators, base generators, etc. are used as the initiators. Of the known generators, the base generators are considered to be most desirable because of their high activity to the polymerization of episulfide compounds. The study of photobase generators are reported in Kagaku Kogyo, vol. 50, pp 592-600 (1999) and J. Polym. Sci. Part A, vol. 39, pp 1329-1341 (2001). However, it is only a short time since the study of the photobase generators was begun, and no photobase generator having a practically acceptable activity has not been found until now.

The major problems of the photobase generators which have been hitherto developed are:

1. since the wavelength range of light absorbed by the photobase generator substantially overlaps that of episulfide compounds which ranges up to about 300 nm, the efficiency of generating base by photolysis is low; and
2. since the base generated by photolysis is weak in basicity, the curing by polymerization of the episulfide compounds is slow.

SUMMARY OF THE INVENTION

Objects of the present invention are to provide a photobase generator with a high activity, a curable composition containing an episulfide compound which is easily curable under ultraviolet irradiation, and a cured product produced by such an ultraviolet irradiation.

As a result of research in view of attaining the above objects, the inventors have found that the compound represented by the following formula 1:

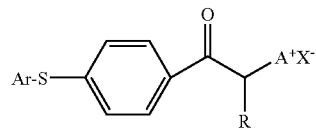

wherein Ar is phenyl, biphenyl, naphthyl or 4-(phenylthio)phenyl, each being optionally substituted with one or more substituents selected from the group consisting of $C_1$-$C_{18}$ alkyl, $C_3$-$C_{18}$ alkenyl, $C_3$-$C_{18}$ alkynyl, $C_1$-$C_{18}$ haloalkyl, $NO_2$, OH, CN, $OR^1$, $SR^2$, $C(=O)R^3$, $C(=O)OR^4$ and halogen wherein $R^1$, $R^2$, $R^3$ and $R^4$ are each hydrogen or $C_1$-$C_{18}$ alkyl; R is hydrogen or $C_1$-$C_{18}$ alkyl; -$A^+$ is an ammonium ion group selected from the group consisting of

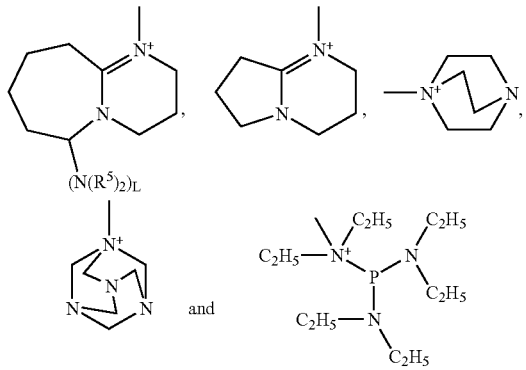

wherein L is 1 or 0 and $R^5$ is $C_1$-$C_5$ alkyl; and $X^-$ is borate anion, N,N-dimethyldithiocarbamate anion, N,N-dimethylcarbamate anion, thiocyanate anion or cyanate anion, absorbs ultraviolet lights of relatively long wavelength (300 nm or longer, preferably 300 to 330 nm) and is photolyzed to generate a strong base efficiently. It has been further found that a composition containing an episulfide compound having at least two thiirane rings in its molecule and the photobase generator represented by the formula 1 is easily cured under ultraviolet irradiation to provide the objective cured product.

DETAILED DESCRIPTION OF THE INVENTION

The photobase generator is represented by the formula 1:

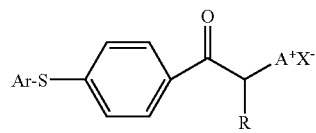

and has an extremely high activity to the polymerization of episulfide compound because it absorbs ultraviolet of relatively long wavelength (300 nm or longer) and is photolyzed to generate a strong base A such as 1,8-diazabicyclo[5.4.0]-7-undecene derivatives, 1,5-diazabicyclo[4.3.0]-5-nonene, triethylenediamine, hexamethylenetetramine and tris(diethylamino)phosphine, represented by the following formulae:

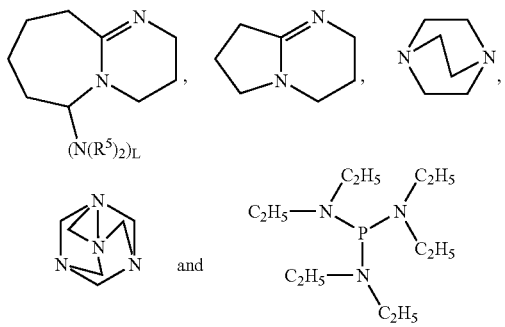

wherein L is 1 or 0 and $R^5$ is $C_1$-$C_5$ alkyl.

In the formula 1, Ar is phenyl, biphenyl, naphthyl or 4-(phenylthio)phenyl. Each of them may be unsubstituted or substituted with one or more substituents selected from the group consisting of $C_1$-$C_{18}$ alkyl, $C_3$-$C_{18}$ alkenyl, $C_3$-$C_{18}$ alkynyl, $C_1$-$C_{18}$ haloalkyl, $NO_2$, OH, CN, $OR^1$, $SR^2$, $C(=O)R^3$, $C(=O)OR^4$ and halogen wherein $R^1$, $R^2$, $R^3$ and $R^4$ are each hydrogen or $C_1$-$C_{18}$ alkyl. Ar is preferably substituted or unsubstituted phenyl, and more preferably unsubstituted phenyl.

R is hydrogen or $C_1$-$C_{18}$ alkyl, preferably hydrogen or $C_1$-$C_3$ alkyl, and more preferably hydrogen.

-$A^+$ is an ammonium ion group selected from the group consisting of

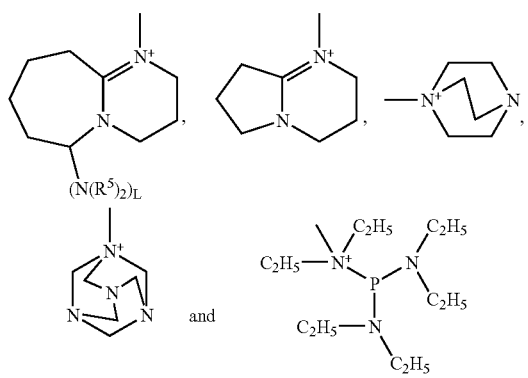

wherein L and $R^5$ are as defined above, and preferably

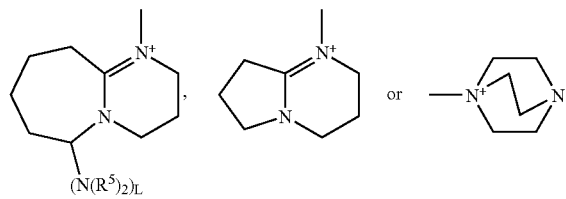

wherein L is as defined above, preferably 0, and $R^5$ is as defined above.

$X^-$ is a counter anion to $A^+$ selected from the group consisting of borate anion, N,N-dimethyldithiocarbamate anion, N,N-dimethylcarbamate anion, thiocyanate anion and cyanate anion, with borate anion being preferred. The borate anion may include tetraphenylborate, methyltriphenyl borate, ethyltriphenylborate, propyltriphenylborate, butyltriphenylborate, pentyltriphenylborate and hexyltriphenylborate.

The photobase generator of the invention may be easily synthesized by known methods as described in J. Polym. Sci. Part A, vol. 39, pp 1329-1341 (2001), etc., for example, by the following synthetic route:

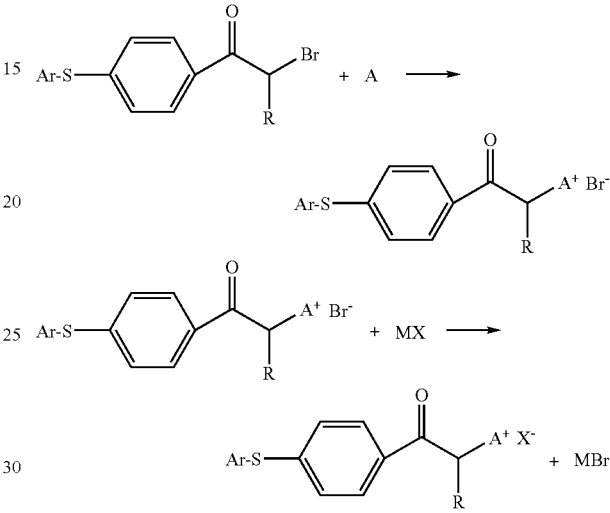

wherein Ar, R, -$A^+$, A and $X^-$ are as defined above and M is alkali metal.

The curable composition of the present invention comprises the photobase generator of the formula 1 and an episulfide compound. The episulfide compound usable in the invention is not specifically limited so long as the episulfide compound has at least two thiirane rings in its molecule, and preferably the episulfide compound represented by the formula 2:

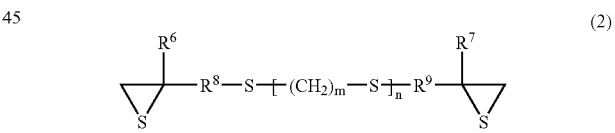

because optical materials having a higher refractive index can be obtained.

In the formula 2, $R^6$ and $R^7$ are each independently hydrogen or $C_1$-$C_{10}$ monovalent hydrocarbon group, preferably hydrogen or $C_1$-$C_3$ monovalent hydrocarbon group, still more preferably hydrogen, and $R^8$ and $R^9$ are each independently $C_1$-$C_{10}$ divalent hydrocarbon group, preferably methylene, ethylene or propylene. The suffix n is an integer from 0 to 4, and the suffix m is an integer from 0 to 6.

Examples of the episulfide compounds of the formula 2 include bis(2,3-epithiopropyl) sulfide, bis(2,3-epithiopropylthio)ethane, bis(2,3-epithiopropylthio)propane, bis(2,3-epithiopropylthio)butane, bis(5,6-epithio-3-thiohexane) sulfide, bis(2,3-epithiopropyl) disulfide, bis(3,4-epithiobutyl) disulfide, bis(4,5-epithiopropyl) disulfide and bis(5,6-epithiohexyl) disulfide, with bis(2,3-epithiopropyl) sulfide (n=0, $R^6=R^7$=hydrogen, and $R^8=R^9$=methylene) and bis(2,3-epithiopropyl) disulfide (n=1, m=0, $R^6=R^7$=hydrogen, and $R^8=R^9$=methylene) being preferred.

The amount of the photobase generator to be used is 0.001 to 50 parts by weight, preferably 0.005 to 30 parts by weight, and more preferably 0.01 to 20 parts by weight based on 100 parts by weight of the episulfide compound.

The curable composition may be added with a sensitizer. By adding the sensitizer, the curable composition is cured with a low energy ultraviolet irradiation. Examples thereof include benzophenone, acetophenone, thioxanthone, anthracene, perylene and phenothiazine, although not limited these compounds so long as the compound can promote the polymerization curing by responding to the ultraviolet irradiation. The amount of the sensitizer, if added, is 0.001 to 50 parts by weight, preferably 0.005 to 30 parts by weight, and more preferably 0.01 to 20 parts by weight based on 100 parts by weight of the episulfide compound.

Some of the photobase generators of the formula 1 are less soluble to the episulfide compounds. In such a case, it is preferred to combinedly use a solvent for the photobase generator. The type of the solvent is not particularly limited so long as the solvent has a high dissolving power to the photobase generator and does not inhibit the polymerization. Examples thereof include lactones such as γ-butyrolactone; ethers such as tetrahydrofuran and diethyl ether; amides such as N,N-dimethylformamide; aromatic hydrocarbons such as toluene; aliphatic hydrocarbons such as hexane; ketones such as acetone and methyl ethyl ketone; esters such as ethyl acetate; alcohols such as isopropyl alcohol; and alkyl halides such as dichloromethane. The amount of the solvent, if used, is preferably 0.1 to 100 parts by weight, more preferably 1 to 30 parts by weight and still more preferably 1 to 20 parts by weight based on 100 parts by weight of the episulfide compound.

To improve the properties such as weatherability, oxidation resistance, mechanical strength, surface hardness, adhesion, refractive index and dyeability, a compound selected from mercaptans, epoxy compounds, iso(thio)cyanates, phenols, amines, sulfur-containing inorganic compounds and selenium-containing inorganic compounds may be added. In case of using these compound, a known catalyst for polymerization curing may be further added, if desired.

The composition may contain filler such as powders, particles and fibrous materials according to the necessity and the end use in an amount not preventing the transmission of light and the progress of polymerization for curing. Examples of the fillers include inorganic compound such as silica, alumina, titania, zirconia and calcium carbonate, and particles of metals such as copper, silver and gold.

The curable composition of the invention is cured by ultraviolet irradiation, for example, under the conditions of illuminance of 1 to 100 mW/cm², temperature of 0 to 100° C. and irradiation time of about one second to about one day, preferably about ten seconds to about one hour. The source of ultraviolet lights may be a high-pressure mercury lamp, an ultra high-pressure mercury lamp, a metal halide lamp, a high power metal halide lamp, etc., although not particularly limited so long as the apparatus generates ultraviolet lights. Since the photobase generator of the formula 1 is incorporated, the curable composition of the invention is cured very promptly. For example, as evidenced by Example 5 described below, the degree of cure reaches two times or more the use of known photobase generators when compared under the same ultraviolet irradiation conditions.

The curing by ultraviolet irradiation is susceptible to inhibition by oxygen. Therefore, the ultraviolet irradiation is carried out in an atmosphere having an oxygen concentration of preferably 3% by volume or less, more preferably 0.5% by volume or less, and still more preferably 0.3% by volume or less.

The curing of the curable composition can be promoted by a heat treatment after the ultraviolet irradiation. Although depending on the degree of cure after the ultraviolet irradiation, the heating temperature is preferably room temperature to 200° C. and the heating time is preferably one minute to three days.

The invention will be explained in more detail with reference to the following examples. However, it should be noted that the scope of the invention is not limited thereto.

EXAMPLE 1

Synthesis of 1-(4'-phenylthio)phenacyl-(1-azonia-4-azabicyclo[2.2.2]octane) tetraphenylborate (I)

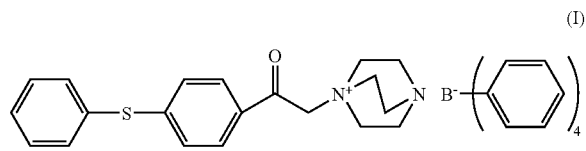

(1) Synthesis of 1-(4'-phenylthio)phenacyl-(1-azonia-4-azabicyclo[2.2.2]octane) bromide In a 100-mL round-bottomed flask, 1.41 g (0.0046 mol) of 2-bromo-4'-phenylthioacetophenone and 20 mL of acetone were stirred to prepare a uniform solution. Then, 20 mL of acetone solution dissolving 0.52 g (0.0046 mol) of 1,4-diazabicyclo[2.2.2]octane was added to the flask at room temperature and the stirring was continued for one hour. The precipitated solid matter was separated by filtration, washed twice with 10 mL of acetone and dried to obtain 1.60 g (0.0038 mol, 83% yield) of white solid, which was identified as the target 1-(4'-phenylthio)phenacyl-(1-azonia-4-azabicyclo[2.2.2]octane) bromide by $^1$H-NMR analysis.

(2) Synthesis of 1-(4'-phenylthio)phenacyl-(1-azonia-4-azabicyclo[2.2.2]octane) tetraphenylborate In a 100-mL round-bottomed flask, 1.00 g (0.0024 mol) of the obtained 1-(4'-phenylthio)phenacyl-(1-azonia-4-azabicyclo[2.2.2]octane) bromide and 20 mL of ethanol were stirred. Then, 20-mL of ethanol solution dissolving 0.86 g (0.0025 mol) of sodium tetraphenylborate was added to the flask at room temperature, and the stirring was continued for one hour. The precipitated solid matter in the flask was separated by filtration and dried to obtain 1.34 g (0.0020 mol, 85% yield) of white solid, which was identified as the target 1-(4'-phenylthio)phenacyl-(1-azonia-4-azabicyclo [2.2.2]octane) tetraphenylborate by $^1$H-NMR analysis.

$^1$H-NMR (δ, ppm), CD$_3$CN 7.77-6.84 (m, 29H, ArH), 4.61 (s, 2H, COCH$_2$), 3.46 (m, 6H, CH$_2$), 3.11 (m, 6H, CH$_2$)

EXAMPLE 2

Synthesis of 1-(4'-phenylthio)phenacyl-(5-azonia-1-azabicyclo[4.3.0]-5-nonene) tetraphenylborate (II)

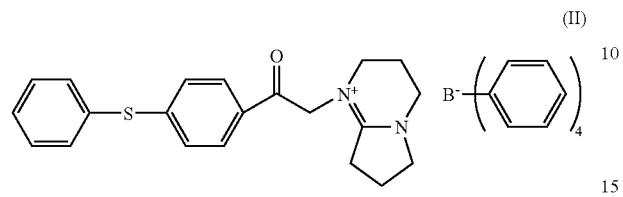

(II)

In a 100-mL round-bottomed flask, 1.74 g (0.0057 mol) of 2-bromo-4'-phenylthioacetophenone and 30 mL of diethyl ether were stirred to prepare a uniform solution. Then, 30 mL of diethyl ether solution dissolving 0.50 g (0.0040 mol) of 1,5-diazabicyclo[4.3.0]-5-nonene was added to the flask under cooling in an ice bath and the stirring was continued for 30 min. The precipitated solid matter was separated by filtration and washed twice with 30 mL of diethyl ether.

The orange solid matter thus obtained and 30 mL of ethanol were placed into a 100-mL round-bottomed flask and stirred. Then, 30 mL of ethanol solution dissolving 0.97 g (0.0028 mol) of sodium tetraphenylborate was added to the flask under cooling in an ice bath, and the stirring was continued for 30 min. The precipitated solid matter in the flask was separated by filtration and dried to obtain 1.67 g (0.0025 mol, 88% yield) of white solid, which was identified as the target compound by $^1$H-NMR analysis.

$^1$H-NMR ($\delta$, ppm), CD$_3$CN 7.82-6.84 (m, 29H, ArH), 4.84 (s, 2H, COCH$_2$), 3.70-3.68 (t, 2H, CH$_2$), 3.38 (t, 2H, CH$_2$), 3.32 (t, 2H, CH$_2$), 2.71 (m, 2H, CH$_2$), 2.15-2.13 (m, 4H, CH$_2$)

EXAMPLE 3

Synthesis of 1-(4'-phenylthio)phenacyl-(8-azonia-1-azabicyclo[5.4.0]-7-undecene) tetraphenylborate (III)

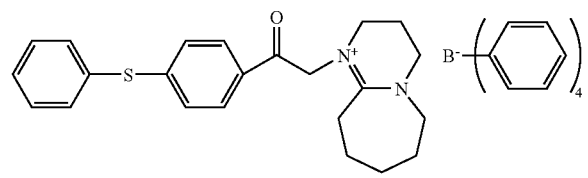

(III)

The target compound was synthesized in the same manner as in Example 2 except for using 1,8-diazabicyclo[5.4.0]-7-undecene in place of 1,5-diazabicyclo[4.3.0]-5-nonene.

$^1$H-NMR ($\delta$, ppm), CD$_3$CN 7.83-6.83 (m, 29H, ArH), 5.02 (s, 2H, COCH$_2$), 3.62 (t, 2H, CH$_2$), 3.51 (t, 2H, CH$_2$), 3.34 (t, 2H, CH$_2$), 2.55 (m, 2H, CH$_2$), 2.16-2.12 (m, 2H, CH$_2$), 1.71 (m, 4H, CH$_2$), 1.58 (m, 2H, CH$_2$)

REFERENCE EXAMPLE 1

Synthesis of 1-phenacyl-(1-azonia-4-azabicyclo[2.2.2]octane) tetraphenylborate (IV)

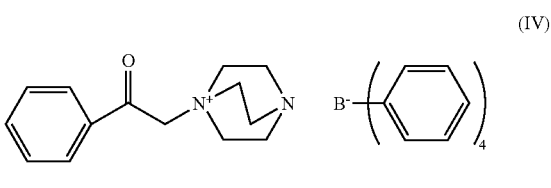

(IV)

The target compound was synthesized in the same manner as in Example 1 except for using 2-bromoacetophenone in place of 2-bromo-4'-phenylthioacetophenone. The compound was identified by $^1$H-NMR analysis.

REFERENCE EXAMPLE 2

Synthesis of 1-naphthoylmethyl-(1-azonia-4-azabicyclo[2.2.2]octane) tetraphenylborate (V)

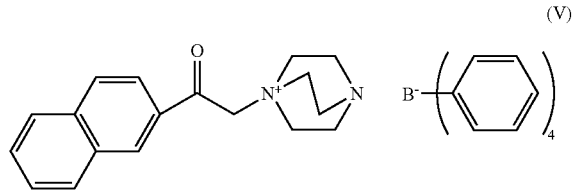

(V)

The target compound was synthesized in the same manner as in Example 1 except for using 2-bromoacetylnaphthalene in place of 2-bromo-4'-phenylthioacetophenone. The compound was identified by $^1$H-NMR analysis.

EXAMPLE 4

Measurement of Molar Absorption Coefficient of Photobase Generator

The photobase generators synthesized in Examples 1-3 and Reference Examples 1 and 2 were measured for molar absorption coefficient $\epsilon$ (254 nm and 313 nm) in the following manners. The results are shown in Table 1. It was found that the compound I efficiently absorbed light of 313 nm.

Measuring Method

Into a 10-mL graduated flask charged with 0.01 g of each photobase generator, acetonitrile was added up to the marked line to prepare a solution. Using a measuring pipette, 1 mL of the solution was put into another 10-mL graduated flask, and then diluted with acetonitrile by a factor of 10. By repeating this procedure, a 100-time diluted solution of the original solution was prepared.

The prepared solution was measured for absorption spectrum at 200 to 400 nm in a quartz cell (1-cm optical path) by a spectrophotometer "UV-2500" available from Shimadzu Corporation. The molar absorption coefficient was calculated from the following equation using the absorbance obtained from the spectrum.

Molar Absorption Coefficient ($\epsilon$)=(Absorbance×Molecular weight)/Concentration (g/L)

TABLE 1

| Photobase Generator | Molar Absorption Coefficient ε | |
|---|---|---|
| | ε (254 nm) | ε (313 nm) |
| Example 1 (Compound I) | 16,000 | 30,000 |
| Example 2 (Compound II) | 11,400 | 20,600 |
| Example 3 (Compound III) | 13,800 | 21,500 |
| Reference Example 1 (Compound IV) | 17,300 | 0 |
| Reference Example 2 (Compound V) | 49,600 | 1,400 |

EXAMPLE 5

Photocuring of Episulfide Compound

Bis(2,3-epithiopropyl) sulfide (100 parts), each photobase generator (2 parts), γ-butyrolactone (6 parts) and silicone oil "KF-351" available from Shin-Etsu Chemical Co., Ltd. (0.2 part) were made into a uniform solution by mixing. The solution was applied onto a glass substrate by using a bar coater (No. 9).

The glass substrate was placed in a chamber having a viewing window made of quartz, and nitrogen was allowed to flow through the chamber. After confirming that the oxygen concentration of the atmosphere in the chamber was reduced to 0.2% by volume, the glass substrate was irradiated with ultraviolet light from a metal halide lamp (30 mW/cm$^2$) for one minute. Immediately after the irradiation, the glass substrate was immersed in tetrahydrofuran (THF) to remove the non-cured components by dissolution. After 30 min of the immersion, the glass substrate was dried. To evaluate the curing speed, the degree of cure was determined from the following equation. The results are shown in Table 2.

Degree of cure (%)=(Weight of resin remained on glass substrate)/(Weight of solution applied onto glass substrate)×100.

The results showed that the episulfide compound was cured at an extremely high speed when the compound I was added.

TABLE 2

| Photobase generator | Degree of cure (%) |
|---|---|
| Compound I | 44.6 |
| Compound IV | 3.6 |
| Compound V | 18.5 |

According to the invention, a photobase generator with high activity, a curable composition containing an episulfide compound which is easily curable under ultraviolet irradiation, and a cured product produced by such an ultraviolet irradiation can be provided.

What is claimed is:

1. A photobase generator represented by the following formula 1:

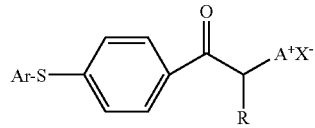

(1)

wherein Ar is phenyl, biphenyl, naphthyl or 4-(phenylthio) phenyl, each being optionally substituted with one or more substituents selected from the group consisting of $C_1$-$C_{18}$ alkyl, $C_3$-$C_{18}$ alkenyl, $C_3$-$C_{18}$ alkynyl, $C_1$-$C_{18}$ haloalkyl, $NO_2$, OH, CN, $OR^1$, $SR^2$, $C(=O)R^3$, $C(=O)OR^4$ and halogen wherein $R^1$, $R^2$, $R^3$ and $R^4$ are each hydrogen or $C_1$-$C_{18}$ alkyl; R is hydrogen or $C_1$-$C_{18}$ alkyl; -$A^+$ is an ammonium ion group selected from the group consisting of

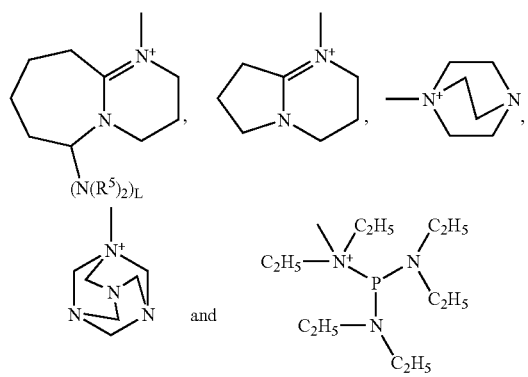

wherein L is 1 or 0, and $R^5$ is $C_1$-$C_5$ alkyl; and $X^-$ is an anion selected from the group consisting of borate anion, N,N-dimethyldithiocarbamate anion, N,N-dimethylcarbamate anion, thiocyanate anion and cyanate anion.

2. The photobase generator according to claim 1, wherein Ar of the formula 1 is phenyl.

3. The photobase generator according to claim 1, wherein -$A^+$ of the formula 1 is an ammonium ion group selected from the group consisting of

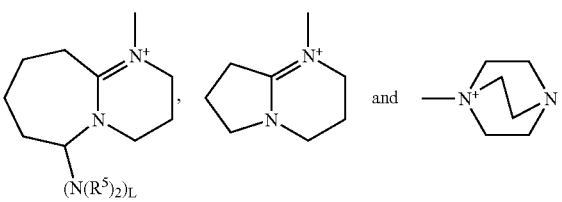

wherein L and $R^5$ are as defined above.

4. The photobase generator according to claim 1, wherein $X^-$ of the formula 1 is borate anion.

5. The photobase generator according to claim 1, which absorbs ultraviolet light of a wavelength of at least 300 nm.

6. A curable composition comprising at least one episulfide compound having two or more thiirane rings in its molecule and at least one photobase generator represented by the formula 1:

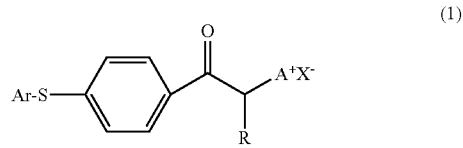

(1)

wherein Ar is phenyl, biphenyl, naphthyl or 4-(phenylthio) phenyl, each being optionally substituted with one or more substituents selected from the group consisting of $C_1$-$C_{18}$ alkyl, $C_3$-$C_{18}$ alkenyl, $C_3$-$C_{18}$ alkynyl, $C_1$-$C_{18}$ haloalkyl, $NO_2$, OH, CN, $OR^1$, $SR^2$, $C(=O)R^3$, $C(=O)OR^4$ and halogen wherein $R^1$, $R^2$, $R^3$ and $R^4$ are each hydrogen or $C_1$-$C_{18}$ alkyl; R is hydrogen or $C_1$-$C_{18}$ alkyl; -$A^+$ is an ammonium ion group selected from the group consisting of

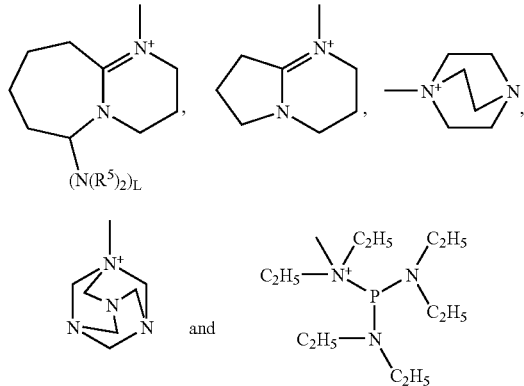

wherein L is 1 or 0, and $R^5$ is $C_1$-$C_5$ alkyl; and $X^-$ is an anion selected from the group consisting of borate anion, N,N-dimethyldithiocarbamate anion, N,N-dimethylcarbamate anion, thiocyanate anion and cyanate anion.

7. The curable composition according to claim 6, wherein Ar of the formula 1 is phenyl.

8. The curable composition according to claim 6, wherein -$A^+$ of the formula 1 is an ammonium ion group selected from the group consisting of

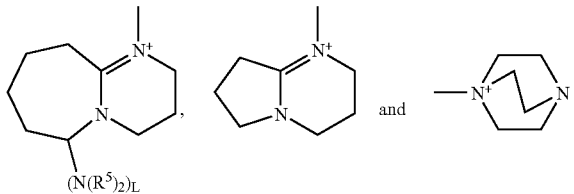

wherein L and $R^5$ are as defined above.

9. The curable composition according to claim 6, wherein $X^-$ of the formula 1 is borate anion.

10. The curable composition according to claim 6, wherein the episulfide compound is represented by the following formula 2:

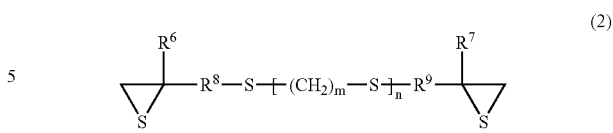

wherein n is an integer of 0 to 4, m is an integer of 0 to 6, $R^6$ and $R^7$ are each independently hydrogen or $C_1$-$C_{10}$ monovalent hydrocarbon group, and $R^8$ and $R^9$ are each independently $C_1$-$C_{10}$ divalent hydrocarbon group.

11. The curable composition according to claim 10, wherein the episulfide compound is bis(2,3-epithiopropyl) sulfide or bis(2,3-epithiopropyl) disulfide.

12. The curable composition according to claim 6, further comprising a sensitizer.

13. The curable composition according to claim 6, further comprising a solvent for the photobase generator of the formula 1.

14. A method of curing which comprises a step of curing the curable composition as defined in claim 6 by ultraviolet irradiation.

15. The method of curing according to claim 14, further comprising a step of curing by heating after the curing step by ultraviolet irradiation.

16. The method of curing according to claim 14, wherein the ultraviolet irradiation is carried out in an atmosphere having an oxygen concentration of 3% or less.

17. The method according to claim 16, wherein the oxygen concentration is 0.3% or less.

18. The method according to claim 14, wherein the curing is carried out in the presence of at least one base represented by the following formulae:

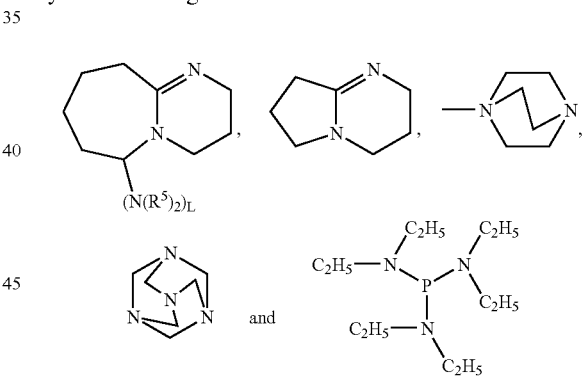

wherein L is 1 or 0, and $R^5$ is $C_1$-$C_5$ alkyl.

19. The curable composition according to claim 6, wherein the composition is capable of being cured by ultraviolet radiation.

* * * * *